United States Patent
Nissani

[19]

[11] Patent Number: 6,164,278
[45] Date of Patent: Dec. 26, 2000

[54] TASTE-BASED APPROACH TO THE PREVENTION OF TEETH CLENCHING AND GRINDING

[76] Inventor: Moti Nissani, 24281 Cloverlawn, Oak Park, Mich. 48237

[21] Appl. No.: 09/257,312

[22] Filed: Feb. 25, 1999

[51] Int. Cl.[7] ............................................ A61F 5/56
[52] U.S. Cl. ......................... 128/848; 128/859; 602/902
[58] Field of Search .................................. 128/846, 848, 128/859–862; 602/902

[56] References Cited

U.S. PATENT DOCUMENTS

| | | |
|---|---|---|
| 1,772,232 | 8/1930 | Van Guilder . |
| 4,211,008 | 7/1980 | Lerman . |
| 4,220,142 | 9/1980 | Rosen et al. . |
| 4,535,724 | 8/1985 | David . |
| 4,669,477 | 6/1987 | Ober . |
| 4,715,367 | 12/1987 | Crossley . |
| 4,934,378 | 6/1990 | Perry . |
| 4,976,618 | 12/1990 | Anderson . |
| 4,979,516 | 12/1990 | Abraham, II . |
| 4,989,616 | 2/1991 | Lee, Jr. . |
| 4,995,404 | 2/1991 | Nemir . |
| 5,078,153 | 1/1992 | Nordlander et al. . |
| 5,137,176 | 8/1992 | Martineau et al. . |
| 5,190,051 | 3/1993 | Wilson . |
| 5,208,085 | 5/1993 | Pace . |
| 5,385,734 | 1/1995 | Friedman . |
| 5,474,093 | 12/1995 | Pettiet . |
| 5,490,520 | 2/1996 | Schaefer et al. . |
| 5,553,626 | 9/1996 | Burger et al. . |
| 5,586,562 | 12/1996 | Matz . |
| 5,620,011 | 4/1997 | Flowers ................................. 128/861 |
| 5,666,973 | 9/1997 | Walter . |
| 5,682,904 | 11/1997 | Stinnett ................................. 128/861 |
| 5,823,193 | 10/1998 | Singer et al. . |
| 5,947,724 | 9/1999 | Frantz ................................... 128/861 |

OTHER PUBLICATIONS

Garcia, J., Ervin, F. R, and Koelling, R. A. Learning with prolonged delay of reinforcement. 1966. *Psychonomic Science* 5: 121–2.

Glaros, A. G., Tabacchi, K. N., and Glass, E. G. Effect of parafunctional clenching on TMD pain. 1998. *Journal of Orofacial Pain* 12: 145–52.

Green, B. G, and Lawless, H. T. The Psychophysics of somatosensory chemoreception in the nose and mouth. 1991. Chapter 12 in: T. V. Getchell et al. *Smell and Taste in Health and Disease*. New York: Raven Press.

Hartmann, E. Bruxism. 1994. Chapter 59 of Kryger, M. H., Roth, T., and Dement, W. C. *Principles and Practice of Sleep Medicine*, 2$^{nd}$ edition. Philadelphia: W. B. Saunders. pp. 598–601.

Hori, A. Twin studies of parasomnias. 1997. In: Meier–Ewert, K. and Okawa, M. (eds.) *Sleep–Wake Disorders,* Chapter 12, pp. 115–123. New York: Plenum Press.

Huang, W., Rothe, M. J., and Grant–Kels, J. M. The burning mouth syndrome. 1966. *Journal of the American Academy of Dermatology* 34(1): 91–8.

Isacsson, G., Barregard, L., Selden, A. and Bodin, L. Impact of nocturnal bruxism on mercury uptake from dental amalgams. 1997. *European Journal of Oral Sciences* 105(3): 251–7.

Josell, S. D. Habits affecting dental and maxillofacial growth and development. 1995. *Dental Clinics of North America,* 39(4): 851–60.

(List continued on next page.)

*Primary Examiner*—Michael A. Brown

[57] ABSTRACT

A new biofeedback modality for the treatment of bruxism. A mildly aversive, safe, liquid is inserted into, and sealed in, small, bilaterally-sleeved, polyethylene capsules. Two capsules are attached to a specially-constructed dental appliance which comfortably and securely places them between the lower and upper teeth. The appliance and capsules are worn at night or at other times when bruxism is suspected to occur. Whenever a sleeping or an awake patient attempts to brux, the capsules rupture and the liquid is released into the mouth. The liquid then draws the patient's conscious attention to, and forestalls, any attempt of teeth clenching or grinding. Variations of the method and device can be used to diagnose bruxism and to sustainably release medications and odor-masking substances into the mouth,.

8 Claims, 2 Drawing Sheets

OTHER PUBLICATIONS

Klineberg, I. Bruxism: aetiology, clinical signs and symptoms. 1994. *Australian Prosthodontic Journal* 8:9–17.

Kydd, W. L. and Daly, C. Duration of Nocturnal tooth contacts during bruxing. 1985. *Journal of Prosthetic Dentistry,* 53(5): 717–21.

Lacrosse, M. B. Understanding change: Five–year follow–up of brief hypnotic treatment of chronic bruxism. 1994. *American Journal of Clinical Hypnosis* 36(4): 276–81.

Lerman, M. D. The hydrostatic splint: new muscle–directed TMJ–PDS treatment technique. 1987. *CDS Review* 80: 30–34.

Long, J. H., Jr. A device to prevent jaw clenching. 1998. *Journal of Prosthetic Dentistry* 79(3): 353–4.

Marbach, J. J., Raphael, K. G., Dohrenwend, B. P., and Lennon, M. C. The validity of tooth grinding measures: Etiology of pain dysfunction syndrome revisited. 1990. *Journal of the American Dental Association* 120: 327–33.

Matthews, E. A treatment for the teeth–grinding habit. 1942. *The Dental Record* 62: 154–5.

McGuire, M. K. and Nunn, M. E. Prognosis versus actual outcome: III. The effectiveness of clinical parameters in accurately predicting tooth survival. 1996. *Journal of Periodontology* 67(7):666–74.

Miguel, A. M. V., Montplaisir, J., Rompre, P. H., Lund, J. P., and Lavigne, G. J. Bruxism and other orofacial movements during sleep. 1992. *Journal of Craniomandibular Disorders: Facial & Oral Pain,* 6 (1): 71–81.

Murray, B. A psychologist investigates what sets people's teeth on edge. 1998. *APA Monitor Online,* 29 (6).

Perel, M. L. Parafunctional habits, nightguards, and root form implants. 1994. *Implant Dentistry* 3: 261–3.

Piccione, A., Coates, T. J., George, J. M., Rosenthal, D., and Karzmark, P. Nocturnal biofeedback for nocturnal bruxism. 1982. *Biofeedback and Self–Regulation* 7(4): 405–19.

Pierce, C. J. and Gale, E. N. A comparison of different treatments for nocturnal bruxism. 1988. *Journal of Dental Research* 67 (3): 597–601.

Pierce, C. J. and Gale, E. N. Methodological considerations concerning the use of Bruxcore Plates to evaluate nocturnal bruxism. 1989. *Journal of Dental Research* 68(6): 1110–4.

Pierce, C. J., Weyant, R. J., Block, H. M., and Nemir, D. C. Dental splint prescription patterns: a survey. 1995 *Journal of the American Dental Association* 126(2): 248–54.

Ploceniak, C. Bruxism and magnesium, my clinical experiences since 1980. 1990. *Revue de Stomatologie et de Chirurgie Maxillo–Faciale,* (French; English abstract in Medline). 1990. 91 Suppl. 1:127.

Quinn, J. H. Mandibular exercises to control bruxism and deviation problems. 1995. *Cranio* 13(1): 30–4.

Rijsdijk, B. A., Van Es, R. J., Zonneveld, F. W., Steenks, M. H., and Koole, R. Botulinum toxin type A treatment of cosmetically disturbing masseteric hypertrophy. 1998. (Dutch; English abstract in Medline). *Nederlands Tijdschrift voor Geneeskunde* 142(10): 529–32.

Rugh, J. D., Barghi, N. and H. Drago, C. J. Experimental occlusal discrepancies and nocturnal bruxism. 1984. *Journal of Prosthetic Dentistry* 51: 548–53.

Rugh, J. D., Graham, G. S., Smith, J. C., and Ohrbach, R. K. Effects of canine versus molar occlusal splint guidance on nocturnal bruxism and craniomandibular symptomatology. 1989. *Journal of Craniomandibular Disorders* 3(4): 203–10.

Sedgwick, J. I hear America grinding. 1995. *Newsweek* 126: 77.

Shatkin, A. J. Bruxism and Bruxomania. 1992. *Rhode Island Dental Journal* 25(4): 7–10.

Takeda, Y., Ishihara, H., and Kobayashi, Y. Influences of occlusal interference on nocturnal sleep and masseter muscle activity. 1989. (Abstract). *Journal of Dental Research* 68: 936.

Tenti, F. V. *Atlas of Orthodontic Appliances.* 1986. Genova, Italy: Microart's for the Caravel.

Thompson, B. H., Blount, B. W., and Krumholtz, T. S. Treatment approaches to bruxism. 1994. *American Family Physician* 49(7): 1617–22.

Trenouth, M. J. The relationship between bruxism and temporomandibular joint dysfunction as shown by computer analysis of nocturnal tooth contact patterns. 1979. *Journal of Oral Rehabilitation* 6: 81–7.

Umberger, F. G. and Van Reenen, J. S. Thumb sucking management: a review. 1995. *International Journal of Orofacial Myology.* 21:41–7.

Watson, T. S. Effectiveness of arousal and arousal plus overcorrection to reduce nocturnal bruxism. 1993. *Journal of Behavior Therapy and Experimental Psychiatry* 24(2): 181–85.

Westrup, D. A, Keller, S. R., Nellis, T. A., and Hicks, R. A. Arousability and bruxism in male and female college students. 1992. *Perceptual & Motor Skills* 75(3): 796–8.

Wiygul, J. P. Maxillary full–coverage appliance. 1991. *Cranio Clinics International* 1(2): 39–53.

Yustin, D., Neff, P., Rieger, M. R., and Hurst, T. Characterization of 86 bruxing patients and long–term study of their management with occlusal devices and other forms of therapy. 1993. *Journal of Orofacial Pain* 7: 54–60.

Ahlin, J. H. Clinical application of remoldable appliances for craniomandibular disorder. 1991. *Cranio Clinics International* 1(2): 65–79.

Bernstein, I. L. Flavor aversion. In Getchell et al., (eds.). *Smell and Taste in Health and Disease.* 1991. New York: Raven Press.

Blount, R. L., Drabman, N. W., Wilson, W., and Stewart, D. Reducing severe diurnal bruxism in two profoundly retarded females. 1982. *Journal of Applied Behavior Analysis* 15: 565–71.

Broughton, R. J. Parasomnias. 1994. In: Chokroverty, S. (Ed.). *Sleep Disorders Medicine,* Chapter 24, pp. 381–99. Boston: Butterworth–Heinemann.

Bubon, M. S. Documented instance of restored conductive hearing loss. 1995. *Functional Orthodontist* 12(1): 26–9.

Budtz–Jorgensen, E. Occlusal dysfunction and stress: An experimental study in macaque monkeys. 1981. *Journal of Oral Rehabilitation* 8(1): 1–9.

Bures, J. Neural mechanisms of conditioned taste aversion revealed by functional ablation procedures. 1993. In: Jurihara, K., Suzuki, N., and Ogawa, H. (eds). *Olfaction and Taste.* Tokyo: Springer–Verlag.

Cassissi, J. E., McGlynn, F. D., and Belles, D. R. EMG–activated feedback alarms for the treatment of nocturnal bruxism: current status and future directions. 1987. *Biofeedback & Self Regulation* 12(1): 13–30.

Chambers, K. C., and Bernstein, I. L. Conditioned flavor aversions. 1995. In Doty, R. L. *Handbook of Olfaction and Gustation,* Chapter 33, pp. 745–73. New York: Marcel Dekker.

Clark, G. T., Koyano, M. S., and Browne, P. A. Oral motor disorders in humans. 1993. *CDA Journal* 21(1): 19–30.

Clarke, J. H. and Reynolds, P. J. Suggestive hypnotherapy for nocturnal bruxism: a pilot study. 1991. *American Journal of Clinical Hypnosis* 33(4): 248–53.

Ellison, J. M. and Stanziani P. SSRI–associated nocturnal bruxism in four patients. 1993. *Journal of Clinical Psychiatry* 54(11): 432–4.

TASTE-BASED APPROACH TO THE PREVENTION OF TEETH CLENCHING AND GRINDING

BACKGROUND: FIELD OF THE INVENTION

The present invention relates chiefly to teeth clenching and grinding and, more specifically, to a method and devices for treating, diagnosing, and preventing bruxism.

BACKGROUND: NATURE AND INCIDENCE OF BRUXISM

Bruxism can be defined as excessive grinding or clenching of teeth. This behavioral pattern is often unconscious and involuntary, and can take place while the patient is asleep or awake.

It is hard to come up with hard figures for the incidence of bruxism. Most people unconsciously grind or clench their teeth now and then, so the key to diagnosis is not the presence or absence of the habit, but such things as its frequency, destructiveness, social discomfort, or physical symptoms (Kydd and Daly, 1985). Moreover, some 80% to 95% of all bruxers are unaware of the habit (Thompson, Blount, and Krumholtz, 1994), or ashamed of it, so they may dismiss evidence that they do in fact engage in self-inflicted wearing away of teeth. Also, it may take years for the first visible signs of worn teeth to appear, yet, in most cases it is these signs which lead to a diagnosis of bruxism. For these reasons, current estimate that 5–20% of all Americans brux may be on the low side.

In any event, and regardless of the exact number, it is inarguably the case that bruxism is a widespread behavioral pattern which adversely affects a significant fraction of the world's population. Thus, there is an urgent need for the development of effective therapies for treating this condition—any advance in this field will help improve the quality of life of millions.

BACKGROUND: CONSEQUENCES AND SYMPTOMS OF BRUXISM

Sleep bruxism often exerts surprisingly powerful forces on teeth, gums, and joints. With no consciousness of the action, and with no food to moderate it, the pressure exerted on teeth can be ten times higher, by some calculations, than the pressure of chewing—powerful enough to crack a walnut (Sedgwick, 1995). While not a life-threatening condition, chronic bruxism often impairs the quality of life of affected individuals. Some suspected symptoms and consequences of this habit will be listed below. (Note: because bruxism is believed to be one of the leading causes [Glaros, Tabacchi, and Glass, 1998] of temporomandibular disorders [TMDs], some symptoms of TMDs will be listed here as well):

- tooth abrasion, fractures, mobility, or loss (McGuire and Nunn, 1996)
- dental caries (grinding or clenching break down the enamel, permitting bacteria to penetrate the dentin, eventually producing a cavity)
- alveolar bone loss
- headaches
- clicking sounds when opening the jaws or while eating
- difficulties in fully opening the mouth
- earaches and hearing loss (for a review and a fascinating case study, see Bubon, 1995)
- adverse, cumulative, irreversible effect on dental implants (Perel 1994) and aesthetic restorations
- neuralgia (an acute paroxismal pain radiating along the courses of one or more nerves)
- tenderness, pain, or fatigue of facial muscles
- diminished facial height which may in turn change one's appearance and cause mandibular overclosure (Thompson, Blount, and Krumholtz, 1994)
- hypertrophy of the masseter muscle, which in turn can adversely affect one's appearance (Rijsdijk et al. 1998), or block the parotid duct and lead to parotitis-like or sialolithiasis-like syndromes (Thompson, Blount, and Krumholtz, 1994)
- higher levels of mercury in the blood (Isacsson et al., 1997) of some bruxers with mercury fillings
- source of annoyance to anyone within hearing range (grinders only; Blount et al., 1982; Watson, 1993).
- over a lifetime, tremendous cost to patient or employer
- reduction in the overall quality of life of long-term sufferers.

BACKGROUND: ETIOLOGY OF BRUXISM

The causes of bruxism are controversial and subject to much theorizing and little hard science (Ellison and Stanziani, 1993; Thompson, Blount, and Krumholtz, 1994). At present, the causes are suspected to be many, to overlap each other, and to vary from one patient to another.

One theory traces bruxism to stress, emotions, and other psychological factors (Murray, 1998; but see Westrup, 1992). There is indeed evidence that stress increases the frequency of bruxing episodes (reviewed in Hartmann, 1994), although this of course does not prove that stress led to the onset of this behavioral pattern in the first place, nor that removal of stress will provide a cure.

The central nervous system may be involved, as is suggested, for example, by the high incidence of bruxism in mentally retarded individuals and by the fact that the uptake of some drugs induces bruxism.

In some cases, bruxism may be traceable to drugs or the excessive consumption of alcohol (Hartmann, 1994). In one study (Ellison and Stanziani, 1993), for example, both the drugs fluoxetine and sertraline were shown to initiate nocturnal bruxism, while buspirone led to its cessation.

Bruxism may be ascribable to a nutritional deficiency (Ploceniak, 1990).

In some cases, bruxism may be traceable to malformations of the jaw or to abnormal dental occlusion (the way the upper and lower teeth fit together when the person closes the mouth; Yustin et al., 1993). Thus, Buds-Jorgensen (1981) showed that artificially-induced malocclusion led to emotional stress and bruxism in monkeys. Similarly, Takeda et al. (1989) showed that the artificial production of occlusal interference in normal subjects in the area of the first molar may have induced bruxism (but see Rugh et al., 1984).

In some cases, bruxism may be a byproduct of dental manipulation of a patient's mouth—the physical handling, the use of removable or fixed dental appliances, or the permanent introduction into the mouth of a variety of foreign substances such as mercury and porcelain. This hypothesis is not borne out by direct evidence, but by the observation that the somewhat related condition of the burning mouth syndrome has been traceable in some cases to denture design faults and to denture material (Huang, Rothe, and Grant-Kels, 1996).

Klineberg (1994) and many others view bruxism as an evolutionary relic, a residue from a remote past when our ancestors needed sharp teeth to defend themselves and retrieve food. A related explanation may view some manifestations of bruxism as a genetically programmed behavioral counterpart of the aging process. Indeed, clinical experience points to a familial pattern (Hartman, 1994). The role of heredity in causing bruxism receives additional support from a higher concordance in the incidence of bruxism among identical twins than among fraternal twins (Hori, 1997, p. 119).

BACKGROUND: DIAGNOSIS OF BRUXISM

The diagnosis of bruxism also presents difficulties. Here it is perhaps convenient to distinguish between grinders and clenchers. In the case of grinders who share living quarters with other people, reports of bruxism might be fairly reliable (but see Marbach et al., 1990). For grinders who live alone, and for clenchers, diagnosis is primarily based on tooth attrition. In the case of both grinders and clenchers, positive proof of bruxing is lacking, and patients may go on disbelieving their dentist or family members for years. It is often only in advanced stages of the disease, when much damage to the teeth has already been wrought, and when TMD or other problems stare them in the face, that many patients concede the existence of a problem. This is exacerbated by their belief that bruxism is rare, by the mistaken belief that it is necessarily a sign of severe emotional problems (witness the original name—still in use in some quarters—bruxomania), and by the insidiously slow process of destruction.

Thus, current diagnostic procedures typically rely on visible damage to teeth, or on devices like the bruxcore plate, which is not necessarily reliable (Pierce and Gale, 1989), and which requires a special appliance, expert analysis, and high costs.

These diagnostic difficulties explain in part the typical neglect of bruxism, at least until some dentition is irreversibly destroyed and the habit is firmly entrenched.

BACKGROUND: TREATMENT OF BRUXISM

Despite almost one century of research, and despite well over one thousand publications on the subject, effective remediation of bruxism still eludes us. Ellison and Stanziani (1993), for example, remark that "no entirely satisfactory treatment has been identified" (p.433/2). Klineberg (1994) says that "the aetiology of bruxism and therefore its management is poorly understood by dentists and their focus on a local dental cause has lead to much unnecessary irreversible dental treatment, with little impact on the incidence of bruxism."

Its seeming simplicity notwithstanding, bruxism indeed presents formidable challenges to both sufferer and therapist. Like snoring, it is unconscious, and hence not under the control of the patient. The symptoms are rarely obvious, and often years elapse between the onset of the problem and its first clinical manifestations. To admit the presence of this problem—in face of the prevailing paradigm in both dental and psychiatric circles—is to concede some serious psychological problems. The most common response therefore is to deny the problem until denial is no longer tenable. Needless to say, by then much irreversible damage has been inflicted, and the habit—regardless of its etiology—is entrenched.

By far the most common treatment regime for bruxism relies on the time-honored procedure (e.g., Matthews, 1942) of interocclusal orthopedic appliances (Rugh et al. 1989). In the United State alone, some 3.6 million nightguards (or occlusal splints) are annually prescribed by dentists in an effort to combat bruxism (1.6 million), myofacial pain (0.9 million), and TMJ pain (1.1 million)—a $1 billion industry (Pierce et al., 1995). Much current research on the treatment of bruxism has been centered on the use of such dental appliances. Many patent applications describe splints for the treatment of bruxism (e.g., U.S. Pat. Nos. 5,666,973 and 5,823,193). Here, a patient is often fitted with a customized, hard acrylic bite guard or splint. At times, the bite guard is made of soft, rubber-like, elastomeric material. Another variation is the hydrostatic splint, a water-bearing pressure-equalizing appliance sold under the commercial name "Aqualizer" and manufactured by Jumar Corp., Arizona (see also U.S. Pat. No. 4,211,008).

It may be worth while to cite the views of several writers on splint therapy: "The most common 'treatment' is a rubber device, worn over the teeth at night, called a mouthguard. This does not actually prevent or cure the bruxism, but it will prevent damage to the teeth when bruxism occurs" (Hartmann, 1994, p. 601). "Occlusal splints worn at night did not significantly reduce bruxing-clenching activity in bruxing subjects" (Kydd and Daly, 1985). Pierce and Gale (1988) found that bruxing decreased by about 50% during two weeks of splint therapy, but that, following withdrawal of treatment, it returned to baseline levels. Klineberg (1994) concludes that occlusal splints "will protect the teeth, but will not alter the habit in the long term." According to Rugh et al. (1989), splint therapy is effective at first, but "the usual trend with longer treatment is to lose its effects. In other words, one usually sees a dramatic decrease or increase in EMG activity the first few nights of splint usage, followed by a gradual return to pretreatment EMG values." The comparative ineffectiveness of the traditional splint is also "borne out by the common clinical finding that patients may bite large teeth marks into night bite guards and frequently fracture appliances" (Trenouth, 1979). Moreover, the use of such splints may sometimes adversely affect the patient's occlusion, e.g., cause an open bite (Ahlin, 1991; Wiygul, 1991).

Many other, less popular, extant approaches to the treatment of bruxism will be mentioned here, although they too are controversial and only provide, at best, partial remediation.

Thus, one intrusive and irreversible dental approach tries to correct malocclusion through orthodontic adjustment of the bite pattern. Yet, the majority of practitioners seem by now to agree that "occlusal equilibriation is costly and relatively ineffective" (Shatkin, 1992).

Another approach involves ingestion of substances such as nutritional supplements, anti-anxiety agents, and muscle relaxers. According to Ploceniak (1990), for instance, prolonged magnesium administration nearly always provides a cure for bruxism. Most authorities, however, feel that, at best, drugs and nutritional supplements are of limited value in the treatment of bruxism, and that they often involve, moreover, untoward side effects.

Still another approach involves psychotherapy and teaching patients how to interrupt muscle tension by relaxing their jaws and breathing deeply (Murray, 1998; see also below). Related and occasionally successful approaches involve hypnotherapy (Clarke and Reynolds, 1991; LaCrosse, 1994), as well as visual imagery and autosuggestion.

Another related and controversial approach is the so-called massed negative practice, a scholarly variation of the folk principle of reverse psychology. Here the patient is told to voluntarily clench the jaw for five seconds, relax it for five seconds, and repeat this procedure five times in succession, six different times a day, for two weeks (Thompson, Blount, and Krumholtz, 1994).

Quinn (1995) suggests isokinetic and stretching exercises of the mandible. Long (1998) describes an apparatus which prevents the creation of vacuum in the mouth; this is based on the belief that vacuum is a necessary condition for jaw clenching.

A more promising approach involves biofeedback. Two variants will be mentioned here. The first, as we have seen, assumes that bruxism is the result of stress, and that stress is often manifested by tense muscles, especially facial muscles. This approach strives to reduce stress by monitoring the tenseness of muscles, and transmitting this information to the patient. Gradually, by becoming alert to the presence of muscle tension, patients develop techniques for reducing that tension, hence stress, and hence, bruxism. Such therapeutic claims are controversial, however, and there is little evidence that they are of much help to the unaware or sleeping bruxer.

The second biofeedback variant assumes, in its simplest terms, that—exact etiology notwithstanding—the habit of bruxism could develop in the first place because it is not accompanied by immediate sensations of pain. In this case, nature failed to provide the pain or awareness signal which often blocks or minimizes self-destructive behavior. This second variant attempts to artificially reintroduce this missing signal.

This variant is often used to treat other disorders. For instance, idiopathic primary enuresis (bedwetting—another sleep disorder) can sometimes be cured by sounding an alarm when urine is released (Broughton, 1994, p. 395; cf U.S. Pat. No. 1,772,232).

This variant is sometimes used to treat bruxism. At times, this involves electromyographic (EMG)-activated alarms (Cassisi, McGlynn, and Belles, 1987; U.S. Pat. No. 4,934,378). One obvious problem with this type of therapy is that "numerous other types of orofacial movements unrelated to bruxism . . . can easily be confused with bruxism if only EMG criteria are used for scoring" (Miguel et al., 1992).

Many United States patents still rely on an alarm system, but take the more reliable bruxing activity itself as their point of departure (U.S. Pat. Nos. 4,220,142; 4,976,618; 4,979,516; 4,989,616; 4,995,404; 5,078,153; 5,190,051; 5,586,562). A commercially available device, the OralSensor, manufactured by Cycura Corp. of Rocklin, Calif., similarly produces an audible tone to make the patient aware that bruxing is taking place.

Feedback approaches employing sound alarms suffer from machine breakdowns and are often unsightly, invasive, intimidating, and expensive; they thus do not lend themselves readily to wide use, and especially not to long-term use. As well, they are only partially effective. In evaluating EMG-activated studies, Pierce and Gale (1988) found that bruxing decreased by about 50% during two weeks of biofeedback therapy, but that, following withdrawal of treatment, the condition returned to baseline levels. Piccione et al. (1982), to cite another example, found that "biofeedback does not appear to be effective in reducing nocturnal bruxing," probably because, over time, subjects learned to ignore the tone and go on sleeping.

In another biofeedback embodiment, bruxism is followed by electrical stimulation to the jaw (U.S. Pat. No. 4,669,477), neck (U.S. Pat. No. 4,715,367), lip (Clark et al., 1993), mouth (U.S. Pat. Nos. 4,995,404; 6,490,520), or tooth (U.S. Pat. No. 5,553,626).

In another interesting psychological approach, the feedback is provided directly by humans, not by machines. In one long-term experiment (Watson, 1993), the spouses of two young people who had recently developed a habit of grinding their teeth were instructed to record the bruxing behavior for a few days, then to alternate periods of not waking their grinding spouse up, waking them up when they heard them grinding, and waking them up followed by overcorrection (a ten-minute period of enforced wakefulness) by the grinding spouse. Follow-up recordings were taken at intervals up to 18 months post-treatment. In both individuals, almost complete cessation of grinding was observed. In a similar study (Blount, 1982), ice was applied to the cheeks of two profoundly retarded diurnal grinders, leading to significant long-term reductions in the incidence of bruxism. But, even if such behavioral approaches are shown to be effective in a large-scale study, they suffer from obvious shortcomings. They are inapplicable to clenchers. Moreover, the four individuals in these two studies may have simply learned to grind inaudibly or to clench instead. Such approaches depend on the presence of another individual nearby, and on the willingness of that individual to provide the needed feedback over a period of many months.

It should be noted that young children typically require different therapeutic approaches from adults. To begin with, the damage to the teeth is transitory, for only the primary teeth suffer damage in this case, not the permanent teeth. Moreover, bruxism in children usually resolves spontaneously. Thus, "observation and reassurance, rather than intervention, are warranted in most cases" (Thompson, Blount, and Krumholtz, 1994).

One feels instinctively that such a seemingly simple behavioral problem as bruxism should be capable of a solution, or at least inexpensive and convenient remediation, especially since the great majority of patients are normal individuals (in my experience, one cannot start a conversation about bruxism in a roomful of people without finding some sufferers of this syndrome who are, one might add, often dissatisfied with existing modes of therapy). Yet an effective treatment program so far is unavailable.

BACKGROUND: CONDITIONED FLAVOR AVERSION

The pioneering studies on conditioned taste aversion (to which this invention owes its greatest intellectual debt) are often attributed to Garcia et al. (1966). By 1993, over 2000 scholarly articles, and dozens of monographs and symposia volumes, have been published in this field (Bures, 1993). Of particular interest in the present context are four key findings (Bernstein, 1991):

First, rats can learn to avoid a particular taste even when they are under deep anesthesia.

Second, the learning is rapid (often involving just one exposure), long-lasting, and resistant to extinction.

Third, such learning is selective. For example, the association between flavors and subsequent gastrointestinal discomfort is more readily learned than the less natural association between sound and gastrointestinal discomfort.

Fourth, humans of all ages (Chambers and Bernstein, 1995) show conditioned taste aversion.

These findings raise the intriguing possibility that unlearned, instinctive flavor aversion can serve in turn as a powerfully aversive, readily associable, stimulus in sleeping humans. Known therapeutic practices lend additional support to this last possibility. Thus, the childhood syndrome of finger sucking, especially when it persists after the permanent teeth begin to erupt, besides being unsightly and unsanitary, can cause severe orthodontic problems, speech defects, psychological problems, and deformation of fingers (Josell 1995). A home remedy of hot sauce or vinegar painted on the finger is a long-standing preventive practice, and commercial solutions containing denatonium benzoate or sucrose octaacetate are also available (U.S. Pat. No. 5,474,093).

SUMMARY, OBJECTS, AND ADVANTAGES

Prior art has been directed to the treatment of bruxism through splints, stress reduction, muscle relaxation, sound alarms, electrical stimulation, drugs, and nutritional supplements. The present invention seeks chiefly to treat bruxism through the more promising, convenient, appealing, safe, and inexpensive procedure of taste aversion. It further seeks to employ the intraoral device(s) of this invention in the diagnosis of bruxism and in the sustained release of other substances. Among the objects of this invention are:

(a) To provide simple, safe, inexpensive means of treating and preventing teeth clenching and grinding.

(b) To provide means of readily diagnosing bruxism.

(c) To provide means of convincing patients that they brux, thereby motivating them to undertake preventive action.

(d) To provide means for the sustained release of medications and odor-masking substances into the oral cavity.

To treat teeth clenching and grinding, an unpleasant-tasting, safe, substance is released into the mouth whenever a patient attempts to brux, thereby drawing the patient's conscious attention to, and forestalling, teeth clenching or grinding. More specifically, the preferred embodiment employs three elements:

an unpleasant-tasting liquid derived from one or more natural or synthetic, palatable, materials such as hot peppers (capsaicinoids), horseradish, quinine, mustard, ginger, garlic, onion, salt, or denatonium benzoate, two small, identical, bilaterally-sleeved, plastic bags, a wrought iron or cast, comfortable, safe, dental appliance which is specially designed to introduce into the mouth, and support therein, the liquid-filled bags More precisely, the liquid in which the unpleasant-tasting substance is dissolved or suspended can be any appropriate solvent such as water, alcohol, vinegar, or other safe, digestible, barely-compressible, fluids. Horseradish extracts, for example, can be suspended in water, alcohol, or vinegar. In all cases, just enough of the aversive substance is used to reach a predetermined level of taste intensity.

The solution is then inserted into, and sealed in, one or more soft- or hard-shelled containers, bags, or capsules. These capsules can be comfortably worn inside the mouth and are made of such materials as polyethylene or wax, which are safe and non-irritating, yet capable of breaking or rupturing when bruxing pressure is applied, thereby releasing their contents into the mouth.

The liquid-filled capsules are then joined to a specially constructed dental appliance. The joined liquid-filled capsules and appliance are inserted into the mouth before going to sleep or whenever teeth clenching and grinding are suspected to occur. The appliance is so designed that the capsules are positioned between the lower and upper teeth and are evenly balanced on each side of the mouth. Whenever the user attempts to brux, the capsules release their disagreeable constituents.

The design and construction of each individual component of the present invention are well-known in the art. The dental appliance, in particular, can come in variety of designs. At present it is molded or cast to fit the mouth of each patient. In the future, a suitable generic design, which fits into the mouths of most patients, may be used.

The appliance and liquid-filled capsules can be used by bruxers wishing to treat their condition, by bruxers and non-bruxers alike to prevent pressure on teeth in special situations when such pressure is particularly counterindicated (e.g., before and after a TMJ or tooth implant operations), or by non-bruxers for a few days to prevent the habit of bruxing from forming in the first place.

In all these conditions and variations, the aversive liquid is released into the mouth under pressure, drawing the patient's conscious attention to, and precluding, teeth clenching or grinding.

To diagnose bruxism and convince patients that they do indeed grind, the sleeved bags of the preferred embodiment may be filled with wax, gum, or some other malleable material. The bags are joined to the same dental appliance as in the treatment variation above. As before, bags and appliance are now inserted into the mouth, so that the capsules are positioned between the lower and upper teeth. Bruxing in turn produces deformations in the impressionable materials, thereby helping to confirm the occurrence of bruxism for both therapist and patient. Thus, both diagnosis and treatment can be effected by essentially the same appliance.

To provide means for the sustained release of medications and odor-masking substances into the mouth, the sleeved bag(s) contain one or more such medications and substances. The bags are again attached to the dental appliance. Bags and appliance are then inserted into the mouth, where the bags sustainably release one or more of the needed medications and odor-masking substances.

In the preferred embodiment of the bruxism treatment program, a customized, safe, minimally-intrusive, dental appliance is constructed. In the confirmatory, diagnostic stage of the program, two identical dental wax pellets are inserted into polyethylene sleeved bags. The bags are then attached to the appliance, which the user wears whenever bruxism is suspected to occur. After the existence of bruxism is confirmed through markings and structural alterations in the wax, the same appliance is used to lodge two identical, small, sleeved, plastic bags filled with a barely-compressible sealed capsaicin solution. When the user clenches or grinds his or her teeth, the pressure within the bag increases and one or two of the bags rupture and wake up the user. The ensuing intraoral release of the aversive, safe, capsaicin whenever bruxing is attempted draws the user's conscious attention to, and forestalls, teeth clenching or grinding. Users then rinse their mouth with cold water, milk, or sucrose/fructose solution, replace the bag(s), and resume sleep. Similarly, when daytime users unconsciously brux, one or two bags rupture, thereby alerting them to the occurrence of bruxing. Users rinse their mouth, replace the bag(s), and resume their activities.

While my invention combines, or improves upon, elements which are known in the prior art, it achieves a radically novel and synergistic result. Despite the tremendous potential of this approach, despite the prevalence of bruxism and its untoward symptoms, despite the fact that bruxism takes place in the mouth and lends itself to taste biofeedback, despite the success of taste aversion in treating other mouth-related conditions such as finger-sucking (Umberger and Van Reenen, 1995), and despite the overwhelming evidence from learning psychology that taste aversion may be particularly suitable to treat sleeping or unaware patients, no one has ever employed a taste modality to treat bruxism. Moreover, the mouth appliance described here has been specifically designed to treat and diagnose bruxism. Moreover, one key segment of prior art references—those involving taste aversion learning—is from an entirely different field. Moreover, theoretical considerations given above, as well as some preliminary clinical data, suggest that the therapy proposed here might well be more effective, more convenient, and cheaper than any current therapeutic device or approach. In particular, Although the invention combines the well-known prior art of extracting and dissolving solids, inserting and sealing liquids in capsules, constructing dental appliances, conditioned flavor aversion (Garcia et al., 1966), taste aversion therapy, and biofeedback, the combination employed in this invention is not implied by, or even imagined in, the prior art. Among the countless articles in these fields, not even one anticipates the advantages of taste aversion in the treatment of bruxism.

The combination proposed herein relies on different and distinct technical fields.

Although the invention herein employs established technologies, it combines them in a unique way such that the results are greater than their constituent elements.

This invention provides the single most promising approach for inexpensively treating a condition which adversely affects the lives of millions.

Upon further study of the specification and appended claims, additional objects, embodiments, and advantages of this invention will become apparent.

BRIEF DESCRIPTION OF THE DRAWINGS

A more complete valuation of the invention and many of its attendant advantages and uses may be realized by reference to the following, sequential views of the preferred embodiment.

REFERENCE NUMERALS IN DRAWINGS

Figure 1:
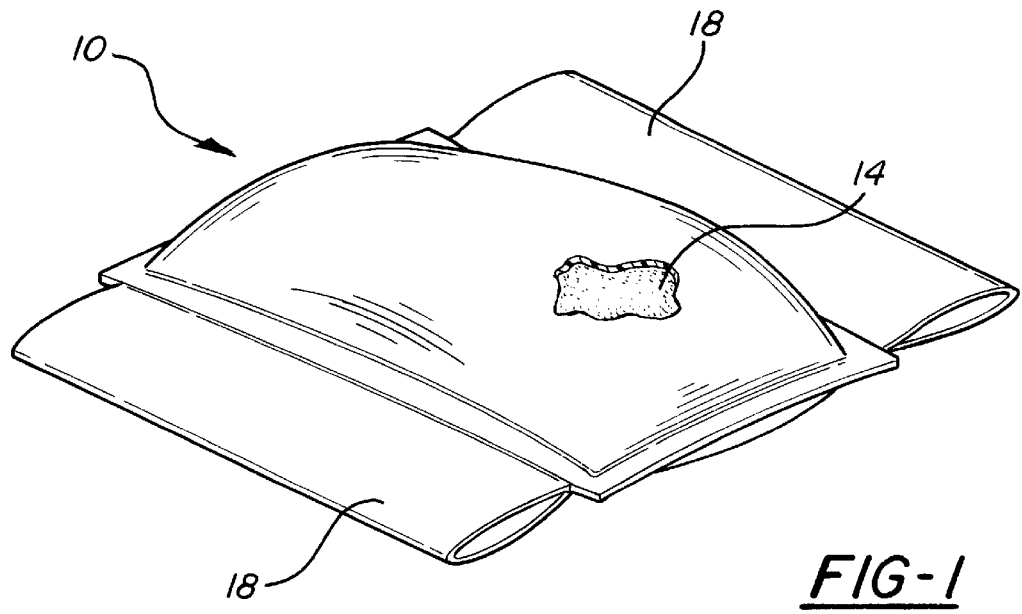
FIG. 1 shows a bilaterally-sleeved capsule.

10 small capsule, container, bag, or reservoir
14 constituents of capsule
18 sleeve of capsule
22 posterior rod of a mandibular dental appliance to which a capsule can be attached
26 curl in one posterior rod to prevent slippage of capsule
30 hinge of appliance to secure it to teeth
34 anterior connection of two sides of appliance

DETAILED DESCRIPTION OF THE INVENTION

All the aversive liquids used in the present invention have one characteristic in common: when released into the oral cavity they produce a sensation strong enough to wake up the sleeping bruxist, and to induce immediate rinsing of the mouth and replacement of the punctured bag(s) with new one(s). The same liquids, albeit less aversive, can be used with awake bruxers.

The substances, which can be used singly or in combination, include table salt, onion, garlic, capsaicin and other members of the capsaicinoids family, horseradish (cf. U.S. Pat. No. 5,485,734), mustard, garlic, onion, zingerone, quinine, or denatonium benzoate. The active ingredients of these substances can in some cases be purchased commercially, or they can be directly extracted by using such suitable solvents as ethyl alcohol, vinegar, or water. The choice of substance, dose, and solvent can be tailored to the needs and preferences of each patient. The choice may be determined as well by individual tastes, e.g., a cauliflower extracts for individuals who detest cauliflowers; a saline solution for patients who need not limit their salt consumption and who prefer mildly aversive substances.

In any given case, the choice of substance(s) and their intensity is subject to ongoing revision. If they are too painful, the intensity is reduced or another substance is tried. If the patient wakes up with ruptured, empty capsules (suggesting that the break-up of the capsules failed to induce arousal), the intensity is raised or other substance(s) are tried.

Turning first to FIG. 1, the preferred embodiment discloses one means of enclosing the aversive substance. It involves small polyethylene bags 10 in which the constituents 14 are enclosed. In the preferred treatment, the constituents comprise a sealed liquid capable of waking a user from deep sleep if the bag ruptures under pressure. Not including the sleeves, the bags are approximately 6 to 13 mm wide, 6 to 25 mm long, and 0.04 to 0.1 mm (about 2.7 mil) thick. They contain little or no air. At their center, the liquid is high enough (roughly from 3 to 7 mm) to rupture the bags when the user clenches or grinds, but is not so high as to seriously inconvenience the user or prevent lip contact. Experience suggests that such bags contain enough liquid to reach many taste buds, but not enough to produce discomfort other than the one associated with unpleasant taste. Each bag contains two sleeves 18, one on each side. The sleeves 18 allow the joining of the bags with the dental appliance.

The manufacture of such bags, capsules, and containers is well known in the art. For instance, U.S. Pat. No. 5,208,085 describes a device for deterring vandalism to exposed exterior surfaces; a device consisting of liquid dye-containing plastic nodules which rupture upon impact. Similarly, U.S. Pat. No. 5,137,176 describes a self-defense method which involves a wax capsule containing concentrated citric acid solution which can be inconspicuously carried in the mouth. In the event of an attack, the user chews through the wall of the wax container, releases the citric acid, and expectorates into the eyes of a would be attacker. Similarly in the present invention, the liquid-bearing capsules may be made of wax and other materials.

Figure 2:
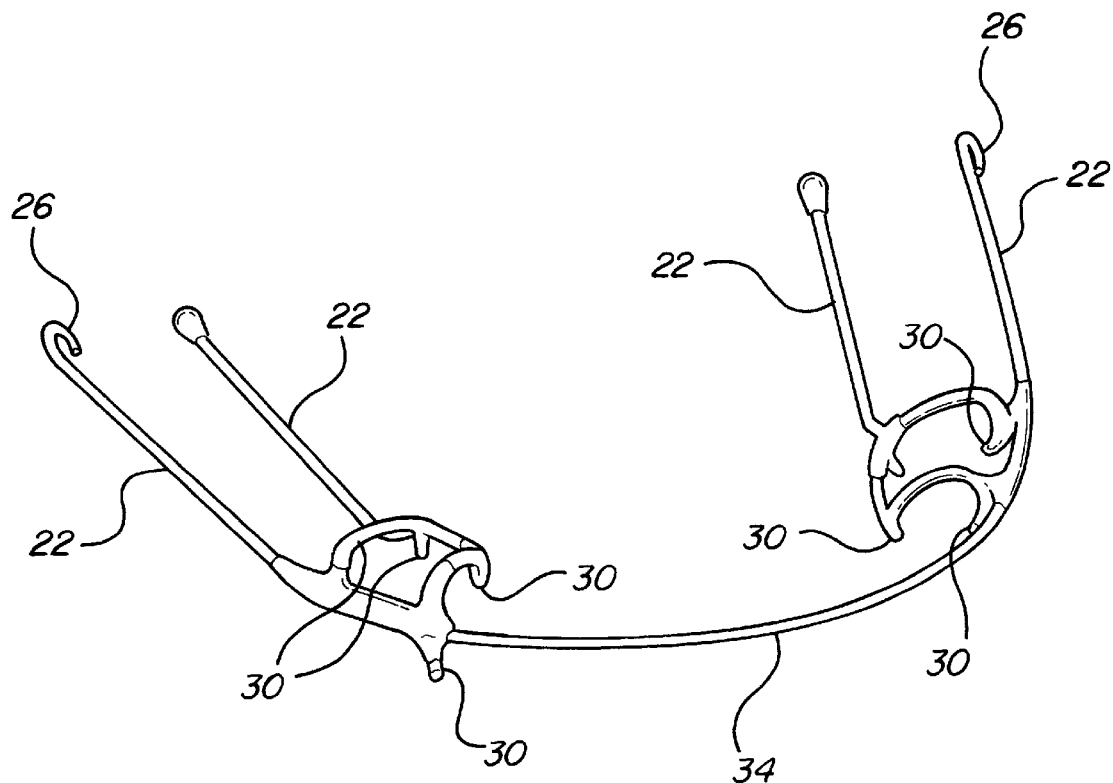
FIG. 2 shows a wrought iron dental appliance.

Turning next to FIG. 2, the invention discloses a dental appliance for securely introducing a pair of objects into the mouth. The appliance is made of two posterior pairs of straight rods 22, of which the exterior one is curled 26 to prevent dislodgment of the bags. Anteriorly, the appliance is provided on each side with a set of soldered four hinges 30 which help keep it comfortably in place. The two sides of the appliance are connected to each other anteriorly 34 to preclude mobility or swallowing of the appliance.

Figure 3:
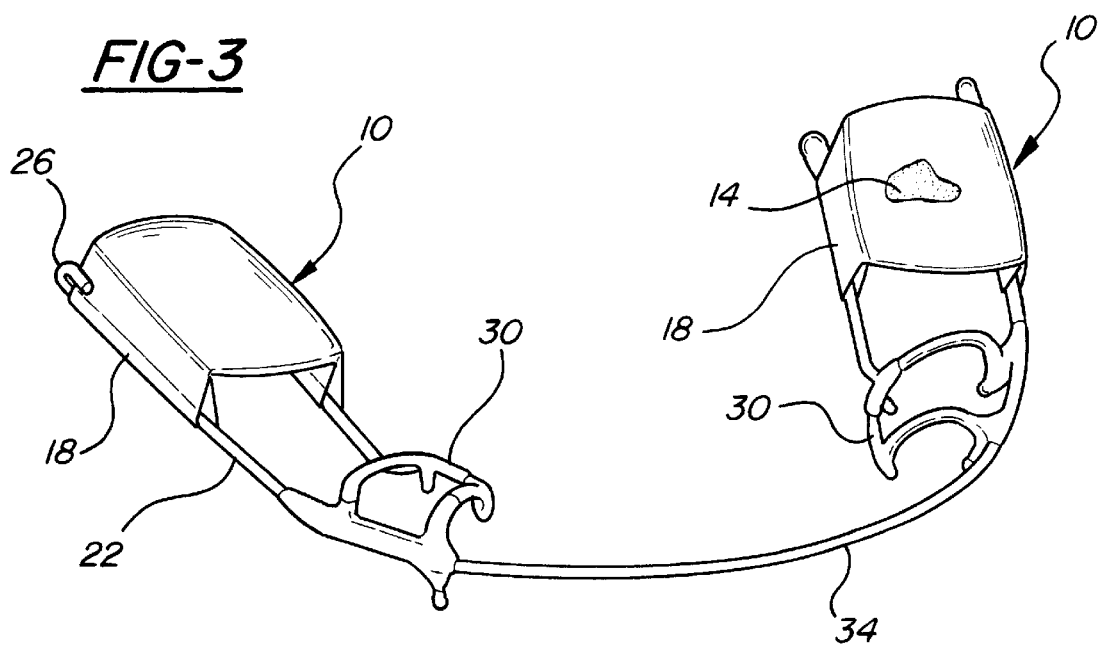
FIG. 3 shows attachments of a pair of capsules of FIG. 1 to the dental appliance of FIG. 2.

Turning next to FIG. 3, the invention discloses the way the liquid-filled 14 containers 10 of FIG. 1 and the appliance of FIG. 2 are joined.

Figure 4:
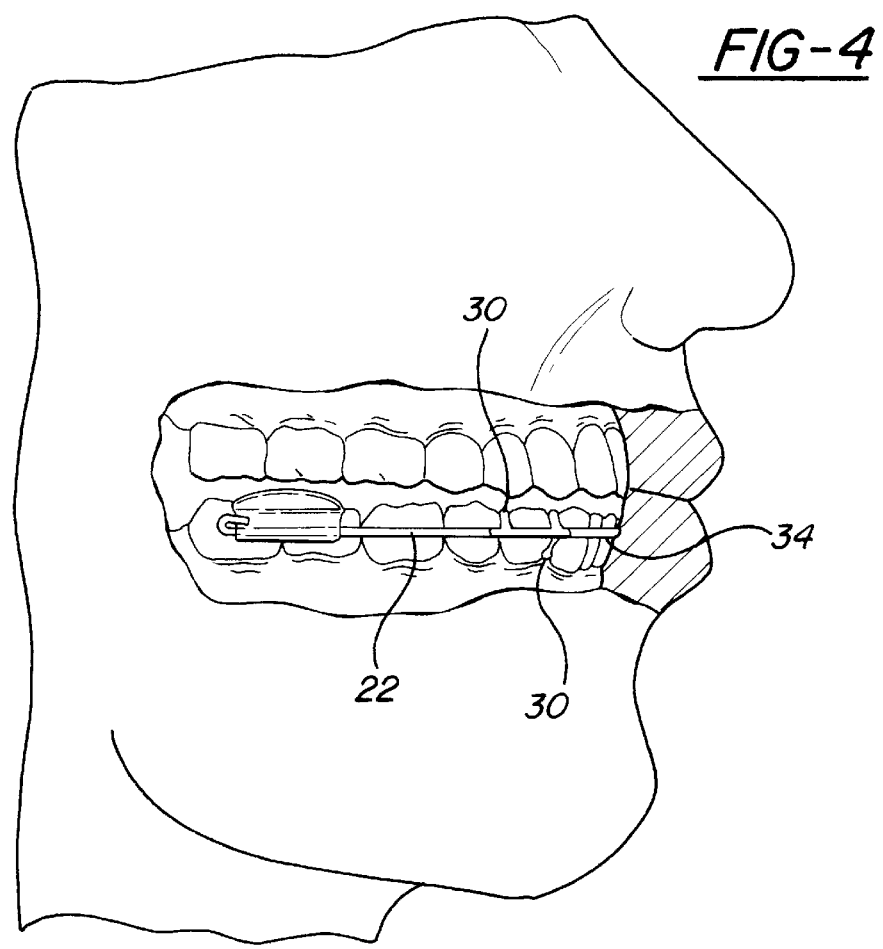
FIG. 4 shows an in-situ placement of the attached capsules and dental appliance of FIG. 3.

Turning now to FIG. 4, the invention discloses the way the complete appliance and containers of FIG. 3 fit into a user's mouth. If bruxing is attempted, one or two of the bags 10 burst, releasing their constituents 14 into the mouth. The sleeping patient wakes up, removes the appliance, rinses the mouth with cold water or other soothing liquid, rinses the appliance with detergent or other suitable solvent, rinses with water, replaces the broken bag(s), reinserts the appliance in the mouth, and goes back to sleep. Alternatively, a second appliance may be used to minimize sleep interruption. An awake user similarly becomes aware of bruxing, rinses mouth and appliance, replaces the bags, reinserts the appliance, and resumes normal activities.

Turning to FIG. 1 again, it is clear that the constituents 14 of the small capsules 10 can be made of wax or other pliable materials which can serve to diagnose or confirm bruxing behavior, and which can help convince the patient of the existence of the problem and of the need for treatment.

Turning to FIG. 1 again, it is clear that the constituents 14 of the small capsules 10 can be made of medications and other substances which require sustained intraoral release, such as nitroglycerin or odor-masking substances.

EXAMPLE 1

One Optional, Extensive, Treatment Program

First Interview

When patients show up at the office, they are asked to fill a questionnaire which places particular emphasis on the history of bruxism, food allergies, nutritional preferences, stress level, and tolerance to such substances as hot pepper, horseradish, or salt.

There follows an interview explaining the nature of bruxism, incidence, and putative causes. In an effort to encourage compliance, motivation, and resolve, particular emphasis is placed on expounding the long-term consequences of bruxism. If the patient evinces sufficient interest, this is followed by an explanation of available treatment approaches, their advantages and pitfalls. If the patient opts for the taste-based approach, the prospective substance(s) and their concentrations are chosen through a trial and error process.

Maxillary and mandibular alginate impressions are taken, and a second appointment is scheduled.

Optional: Suspected audible nighttime grinders may be given a sound-activated tape recorder (which is activated at 53 dB or less), asked to use it for 3–5 nights at home, and, on each morning, to listen to it and record the duration of audible grinding. This optional step establishes a baseline. It also serves as an awareness and motivational tool—after listening to oneself grind, one can no longer deny grinding and one gains a better appreciation for the plight of one's sleeping companions.

Second Interview

On the second interview the appliance is fitted. The patient is given a week's supply of waxy pellets and instructed to attach a fresh pair to the appliance every night before going to sleep (for nocturnal bruxers), or at any other time when bruxing is suspected or known to occur. At this time, care of the appliance, and means of disinfecting it, are discussed. At this time as well, grinders return the tape recorders and discuss their grinding log with the clinician.

Third Interview

A week later the patient returns with the waxy pellets and the evidence for bruxism is analyzed by comparing these pellets to unused ones. This step serves to confirm the condition. It also helps to convince the patient that a potentially serious problem exists. The patient proceeds to the treatment phase itself only after clear evidence of bruxing is obtained (flattened and corrugated pellets). Lack of evidence is open to at least two interpretations. First, the patient may not be a bruxer, in which case no treatment is necessary. Second, it is very likely that the introduction of the appliance—just like the introduction of a splint—temporarily diminishes or eliminates bruxing behavior (Rugh et al., 1984). Such patients continue to wear the diagnostic appliance until there is clear indication that bruxing resumes.

If evidence of bruxing is observed, the same dental appliance is fitted with two bags of water and the patient is asked to grind or clench his/her teeth (depending on the suspected problem) to make sure that this causes one of the bags to burst. This is repeated several times. As a final step, the patient attaches the appliance to a pair of bags filled with the agreed-upon aversive liquid, and attempts to grind or clench. If the taste is subjectively deemed not too painful, yet sufficiently strong to wake the patient during sleep (or to draw attention to the problem for a day bruxer), the patient is given a supply of liquid-filled bags and proceeds to the treatment phase.

At-Home Treatment Program

From that point on, the patient's progress is monitored about once a week, typically through phone consultation, e-mail, or face-to-face interviews.

Particular attention is paid throughout the treatment to the capacity of the liquid to wake the patient from deep sleep, and to the similar problem of habituation (but see Green and Lawless, 1991). If the patient wakes in the morning and finds that the bags have ruptured during the night without causing arousal, the intensity of the favor is increased, or a switch is made to a new substance or to a combination of substances.

When a bag ruptures, the sleeping patient wakes up, rinses his/her mouth with cold water, washes the appliance, replaces the bag(s), and goes back to sleep. A wakeful patient is instructed to act in like manner, but to resume his/her prior activities.

If and when bruxism nearly ceases (two or less bursts per week), the patient continues wearing the appliance for a few more months.

Before discontinuing use, the patient reverts for one week to wearing the appliance with the wax pellets. If little or no evidence of bruxism is seen, the treatment discontinues.

If bruxing behavior is suspected to have returned, the prophylactic measures resume.

The present invention focuses on a taste-based procedure of preventing unconscious clenching and grinding. To achieve a more lasting effect, it may sometimes be necessary to combine the taste-based approach with other treatment modalities.

Needless to say, most patients and therapists might skip many of the time-consuming steps above, focusing, rather, on the indispensable elements the my taste-based approach.

EXAMPLE 2

Case History of One Patient

A 51-year-old man had been told by three dentists over a period of twelve years that his molars were showing signs of bruxism. The patient himself was unaware of the problem and his spouse has never heard him grind his teeth. He ignored the problem for a few years, but became concerned when visible damage (flat short back teeth and crowns) became obvious. Four different dental appliances were tried (a partial, a hydrostatic splint, a soft mandibular splint, and a hard maxillary splint), but they were uncomfortable to wear. As well, the mandibular hard splint permanently and irreversibly damaged the patient's occlusion (changing his bite from a near-perfect one to an annoying open bite) and was particularly hard to clean. Still wearing the hard splint, the patient began to experience the characteristic TMD click and sore jaws, especially upon waking. This was followed by frequent and severe short (5 seconds or less) daytime aches inside his right ear. The pain developed in the right ear only and was particularly sharp and intense. There was no associated vertigo. A subsequent examination revealed a modest degree of hearing loss. At this point, the patient sought the advice of two dentists, a family physician, and two ear-nose-throat specialists. Neither the patient nor these specialists traced the bouts of earaches to the known condition of bruxism. Following their recommendations, he had tried ear drops and spice therapy, but declined a recommendation to undergo rhinoplasty.

At that point the patient replaced the traditional splint with our appliance. The first few nights were stressful, but soon he got used to the idea and slept soundly, while the incidence of arousal episodes rapidly declined. By the third month, a bag would explode and wake him up only about twice a week, often at the point of just falling asleep. Although the patient kept careful records, no obvious correlation to emotional stress was discerned in this case. At this writing, the patient has been wearing the appliance for three months, during which time bruxing was impossible and the earaches and sore jaws vanished.

The patient claims a significant improvement in the quality of his life as a result of using our taste-based approach and being able to control, for the first time in twelve or more years, this destructive and frustrating habit. The patient was particularly concerned about the numbing earache, the possibilities of premature hearing loss (which he felt might be traceable to bruxing), developing a temporomandibular disorder (TMD), and continuing to spend thousands of dollars on crowns and fillings, which events now appear far less likely.

No negative side effects are reported in this case, aside from the inconvenience, especially during the second week, of sleep interruptions when the bags burst, and, to a lesser degree, the mild discomfort caused by the spicy liquid itself (pepper-derived capsaicinoids in his case). Because he found the appliance of this invention far more comfortable and hygienic than the mouthguard he was wearing until then, wearing an appliance posed no problems for him.

OTHER APPLICATIONS, VARIATIONS, AND USES OF THE INVENTION

1. It may be impossible, inconvenient, or undesirable in some instances to lodge the unpleasant-tasting liquid in the mouth. If so desired, the container may be located outside the oral cavity and the liquid conveyed into the oral cavity when the patient bruxes. A similar procedure had been described in U.S. Pat. No. 4,535,724, disclosing a device which facilitates horse training through the introduction of sweet and bitter substances into the horse's mouth.

2. Our preferred embodiment employs an all-or-nothing variant: beyond a certain point, the entire contents of one of the bags spill out. In some situations, however, a slow, sustained release under pressure may be preferable. With appropriate modifications well-known in the art, the present invention lends itself readily to such use.

3. In some cases, it may be desirable to employ a different configuration of the liquid-filled containers. One may, for instance, employ one sealed container inside another. The interior container may contain horseradish particles suspended in vinegar, while the exterior, more resilient, container may contain baking soda. If now tooth pressure is applied, the interior container bursts and the vinegar and baking soda chemically react to release carbon dioxide. The gas pressure then (depending on particular design) either expands the bag to uncomfortable proportions without releasing the liquid, or else ruptures and releases the spicy vinegar into the mouth. In either case, the patient wakes up and replaces the bag.

4. While the invention's chief object is a treatment for bruxism, it can be used to prevent teeth grinding and clenching in other circumstances. For instance, it is particularly important, following such surgical procedures as TMJ operations and implantations of artificial teeth, to prevent any pressure on teeth. The appliance described herein can be used to virtually eliminate such pressure.

5. In view of the surprisingly high incidence of bruxism, it may be worth while to prevent the development of the habit in non-bruxers. The taste-based approach described here can be used as a short-term precautionary measure by non-bruxers to reinforce the habit of keeping teeth apart while not chewing or swallowing.

6. U.S. Pat. No. 4,039,653 describes a device for the sustained release of substances required to mask bad breath and for medications such as local anesthetics, antihistamines, and nitroglycerin. The dental appliance described herein, along with its associated sleeved containers, can be used to accomplish the same goal.

From the foregoing description, one skilled in the art can easily ascertain the essential characteristics of this invention and make various modifications. In particular, the types and combinations of unpleasant-tasting substances, the durable but pressure-sensitive containers associated therewith, the dental appliance to which these containers are attached (Tenti, 1986), the therapeutic approach outlined here, and the types and forms thereof, can be varied within a wide range and using many combinations of substances, vessels, appliances, and approaches, without departing from the spirit and scope of the invention. Hence, the foregoing should be construed as merely illustrative and not restrictive of the scope of the invention.

What I claim is:

1. A method of treating bruxism, comprising means for the intraoral release of an unpleasant-tasting, safe, substance whenever a patient attempts to brux, whereby said substance draws the patient's conscious attention to, and forestalls, teeth clenching or grinding.

2. The method of claim 1 wherein said substance is selected from a group comprising:
   a) naturally occurring materials such as hot peppers, salt, horseradish, quinine, mustard, ginger, garlic, and onion,
   b) synthetic substances such as denatonium benzoate,
   c) a plurality of natural, synthetic, or natural and synthetic, substances.

3. The substance of claim 2 wherein said substance is dissolved or suspended in a liquid selected from a group comprising water, alcohol, vinegar, and other safe, digestible, barely-compressible, fluids to achieve a predetermined level of taste intensity.

4. The liquid of claim 3 wherein said liquid is inserted into and sealed in one or more containers, bags, reservoirs, or capsules, wherein said capsules
   a) can be comfortably worn inside the mouth,
   b) are constructed from such breakable-under-pressure, soft or hard materials, as polyethylene or wax, c) are filled with unpleasant-tasting liquid.

5. The liquid-filled capsules of claim 4 wherein said capsules are joined to a dental appliance, said dental appliance being adapted to fit into the mouth and to support said liquid-filled capsules.

6. The joined liquid-filled capsules and appliance of claim 5, wherein,
   a) said capsules and appliance are inserted into the mouth of a patient,
   b) said capsules are positioned between the lower and upper teeth, and
   c) said capsules are evenly balanced on each side of the mouth,
   whereby said capsules release their disagreeable constituents whenever the patient attempts to brux.

7. The dental appliance of claim 5 wherein said dental appliance is selected from a group comprising
   a) appliances molded or cast to fit the mouth of each patient, and
   b) appliances manufactured to fit into the mouths of most patients.

8. A method of treating and/or preventing bruxism in a patient, comprising:
   inserting a dental appliance adapted to fit in the mouth of the patient and to support breakable-under-pressure liquid-filled capsules in the mouth of the patient, the liquid-filled capsules being positioned between the lower and upper teeth of the patient so that the liquid-filled capsules are evenly balanced on each side of the mouth, the liquid-filled capsules containing an unpleasant-tasting safe, substance dissolved or suspended in a liquid that is placed in the mouths of
   a) bruxers to treat their condition,
   b) bruxers and non-bruxers to prevent pressure on teeth in situations such as those arising after TMD or tooth implant operations, when such pressure is particularly counterindicated,
   c) non-bruxers for a few days to prevent the habit of bruxing from developing in the first place,
   whereby the liquid is released under pressure, drawing the patient's conscious attention to, and precluding, teeth clenching or grinding.

* * * * *